United States Patent
Giojalas et al.

(10) Patent No.: US 8,993,310 B2
(45) Date of Patent: Mar. 31, 2015

(54) DEVICE FOR DIAGNOSIS OF PHYSIOLOGIC STATUS AND/OR SELECTION OF THE BEST SPERMATOZOA OF A SEMEN SAMPLE BASED ON CHEMOTAXIS, AND PROCEDURE OF USE THEREOF

(75) Inventors: Laura Cecilia Giojalas, Córdoba (AR); Héctor Alejandro Guidobaldi, Córdoba (AR); Laura Virginia Gatica, Córdoba (AR); Maria Eugenia Teves, Glen Allen, VA (US); Maria del Mar Montesinos, Prov. de Córdoba (AR); Diego Rafael Uñates, Córdoba (AR)

(73) Assignees: Consejo Nacional de Investigaciones Cientificas y Technicas (CONICET), Buenos Aires (AR); Inis Biotech LLC, Milford, DE (US)

( * ) Notice: Subject to any disclaimer, the term of this patent is extended or adjusted under 35 U.S.C. 154(b) by 0 days.

(21) Appl. No.: 13/254,591
(22) PCT Filed: Mar. 3, 2010
(86) PCT No.: PCT/IB2010/050923
§ 371 (c)(1),
(2), (4) Date: Nov. 9, 2011
(87) PCT Pub. No.: WO2010/100615
PCT Pub. Date: Sep. 10, 2010

(65) Prior Publication Data
US 2012/0094322 A1   Apr. 19, 2012

(30) Foreign Application Priority Data
Mar. 3, 2009   (AR) ................................ P090100749

(51) Int. Cl.
*C12M 1/34* (2006.01)
*C12M 3/00* (2006.01)
(Continued)

(52) U.S. Cl.
CPC ............ *G01N 33/5091* (2013.01); *C12N 5/061* (2013.01); *C12N 5/0612* (2013.01);
(Continued)

(58) Field of Classification Search
CPC .................... G01N 33/5029; G01N 2800/367; B01L 2300/042
USPC .............................. 435/288.5, 288.7; 422/568
See application file for complete search history.

(56) References Cited

U.S. PATENT DOCUMENTS 5,744,366 A * 4/1998 Kricka et al. ................... 436/63
5,849,713 A   12/1998 Eisenbach
(Continued)

FOREIGN PATENT DOCUMENTS

WO   94/15630   7/1994
WO   01/60968 A1   8/2001

OTHER PUBLICATIONS

Fabro, G., et al., "Chemotaxis of Capacitated Rabbit Spermatozoa to Follicular Fluid Revealed by a Novel Directional ty-Based Assay", Biology of Reproduction, vol. 67, pp. 1565-1571, (2002).
(Continued)

*Primary Examiner* — William H Beisner
(74) *Attorney, Agent, or Firm* — Nath, Goldberg & Meyer; Tanya E. Harkins; Joshua B. Goldberg (57) ABSTRACT

A device for diagnosis of physiologic status and/or selection of best spermatozoa of a semen sample based on chemotaxis, and the procedure of thereof, enabling by a simple and inexpensive device the diagnosis and selection of the best spermatozoa in only one step. Only needed are: the present device, a regular light microscope, and personnel with elementary knowledge of laboratory management. The device is of the type having two communicated compartments (1a, 1b), and where said compartments (1a, 1b) communication occurs through a duct or bridge (2) located in the lower part, and above the lower level of mentioned compartments (1a, 1b); in the entrances of said compartments (1a, 1b) appropriate closing means (3, 4) and appropriate air output ducts (5) are placed communicating the top end of compartments (1a, 1b) with the exterior.

6 Claims, 7 Drawing Sheets

(51) Int. Cl.
*G01N 33/50* (2006.01)
*C12N 5/076* (2010.01)
*C12N 5/071* (2010.01)

(52) U.S. Cl.
CPC ........ *G01N33/5029* (2013.01); *G01N 33/5088* (2013.01); *C12N 2501/39* (2013.01); *G01N 2800/367* (2013.01)
USPC .................................... 435/288.5; 435/288.7

(56) References Cited

U.S. PATENT DOCUMENTS

2004/0166569 A1* 8/2004 Marziali et al. .............. 435/91.2
2008/0299537 A1* 12/2008 Eisenbach et al. ................ 435/2

OTHER PUBLICATIONS

Guidobaldi, H.A., et al., "Progesterone from the Cumulus Cells Is the Sperm Chemoattractant Secreted by the Rabbit Oocyte Cumulus Complex", PLoS One, vol. 3, No. 8, e3040, pp. 1-9, (2008).

Koyama, S., et al., "Chemotaxis Assays of Mouse Sperm on Microfluidic Devices", Anal. Chem., vol. 78, pp. 3354-3359, (2006).

Kricka, L.J., et al., "Applications of a Microfabricated Device for Evaluating Sperm Function", Clin. Chem., vol. 39, No. 9, pp. 1944-1947, (1993).

Teves, M.E., et al., "Progesterone at the picomolar range is a chemoattractant for mammalian spermatozoa", Fertility and Sterility, vol. 86, No. 3, pp. 745-749, (2006).

\* cited by examiner

DEVICE FOR DIAGNOSIS OF PHYSIOLOGIC STATUS AND/OR SELECTION OF THE BEST SPERMATOZOA OF A SEMEN SAMPLE BASED ON CHEMOTAXIS, AND PROCEDURE OF USE THEREOF

TECHNICAL FIELD OF THE INVENTION

The present invention refers to a device for diagnosis of physiologic status and/or selection of the best spermatozoa of a semen sample based on chemotaxis, and the procedure of use thereof, enabling through a simple and inexpensive device reach a diagnosis and select the best spermatozoa in one step. Only needed is this device, a regular light microscope, and personnel with elementary knowledge of laboratory handling.

STATE OF THE ART

Sperm cell chemotaxis is a cell transport mechanism guiding spermatozoa to an attractant concentration gradient. In the last few years, efforts have been made to differentiate chemotaxis from a cell aggregation process mediated by other mechanisms.

The chemotaxis process has been identified in different mammal species, for example humans, mice, rabbits, and others.

On the other hand, it is known that progesterone is the main egg microenvironment steroid at the ovulation time, and it has been demonstrated to be a spermatozoa attractant.

Patents PCT WO 02/090373, WO 00/09648, and WO 99/66331 disclose methods and devices to assess spermatozoa chemotaxis, basically comprising two filter-separated vertical compartments, where the attractant is place in the lower and spermatozoa in the top one. Secondary usefulness of the device should be chemotaxis assessment, based on spermatozoa aggregation obtained after some time in the compartment containing the attractant. This methodology does not allow for differentiation of chemotaxis from other cell aggregation provoking processes.

Patent PCT WO 2005/027634 suggests another method to isolate capable spermatozoa. Sperm selection is performed based on sperm cell capability to respond to a temperature gradient, that is, swimming from a colder to a warmer place. The device has an external differential warming system for the fluid of each compartment. Each compartment requires temperature regulation with a difference of only 2° C. between both, placed at a 1 mm distance. This physical feature is obtained by additional thermal equipment, notably making this device manipulation. Enrichment efficiency is 10%.

Patent WO 2005/009222 suggests a method for diagnosis only of the physiologic status of a semen sample based on detection the level of capable spermatozoa. The invention proposes a protocol involving cell death, only serving to diagnose a sample, since capable spermatozoa cannot be recovered for later use in assisted fecundation.

BRIEF DESCRIPTION OF THE INVENTION

The present invention shows a device for physiologic status diagnosis and/or spermatozoa selection from a semen sample based on chemotaxis, of the type having two communicated compartments (1a, 1b), wherein said compartment communication (1a, 1b) occurs through a duct or bridge (2) located at the bottom, and above the lower level of the mentioned compartments (1a, 1b); locating on the entrances of said compartments (1a, 1b) appropriate closing means (3, 4) and appropriate air output ducts (5) communicating the compartment top ends (1a, 1b) with the exterior. Said closing means (3, 4) comprises a plug with a projection (3) and an elastic ring (4) preferable of rubber, and said compartments (1a, 1b), bridge (2) and air output ducts (5) are formed in a transparent body of biocompatible material.

The present invention shows a procedure for physiologic status diagnosis and/or selection of the best spermatozoa of a semen sample based on chemotaxis, comprising the performance of the following stages:

a) place a closing means (3a) in one of the compartments (1a);

b) fill the bridge (2) pouring culture medium through the remaining compartment (1b);

c) place the spermatozoa suspension in compartment (1b) without closing means and placing the closing means (3b);

d) extract the closing means (3a) from the first mentioned compartment (1a) and filling with culture medium or attractant medium;

e) incubate the device;

f) recover the compartment solution (1a);

In an embodiment variation of the former procedure, it is possible to add the following stages: g) place a plug in said compartment (1a); h) unplug compartment (1b); and i) recover the compartment solution (1b).

BRIEF DESCRIPTION OF THE FIGURES

For a better understand of the object of the present invention, it has been schematically illustrated, in its preferred embodiment, assuming a characteristic of demonstrative example, where:

Additional tests were performed to verify that sperm separation occurs by chemotaxis and not by other sperm mechanisms (for example, hyperactivation, chemokinesis, etc.).

Results of FIGS. 8 to 12 confirm that spermatozoa aggregation by the inventive invention is caused by chemotaxis.

One application of the invention is using the method for diagnosis of physiologic status and/or selection of the best spermatozoa of a semen sample.

FIG. 13 shows Enrichment Rate in capable spermatozoa before and after sperm separation. Values depict Mean±SEM (n=9), where the value before sperm separation represents 100%, from which the times capable spermatozoa proportion increased is estimated after sperm separation by chemotaxis. In semen samples defined as normal, ratio of capable spermatozoa obtained after sperm separation by the invention is increased in an average of 200% (*p<0.05 vs. before separation). When the invention is applied to sub-fertile patients samples (T: terato-zoospermic, A-T: asteno-terato-zoospermic, O: oligo-zoospermic, ESCA: sterility of no apparent cause), after sperm separation it is possible to obtain a capable spermatozoa enrichment rate similar to that found in normal samples. That is, independently of the semen sample pathology, the invention use allows quality improvement of sub-fertile samples.

FIG. 14 shows a range of maximum and minimum enrichment rate values of capable spermatozoa reached after sperm separation ("After"), performed with the invention in normal (n=8) and sub-fertile patients semen samples (T: terato-zoospermic, n=29; A-T: asteno-terato-zoospermic, n=15; O: oligo-zoospermic, n=2; ESCA: sterility of no apparent cause, n=3). In normal samples, it is found that they all improve the enrichment rate at least in 100%, compared to before separation, even exceeding values before separation in up to 600%. It is also found that although all pathological samples achieved a capable spermatozoa enrichment exceeding the one found before ("Before") sperm separation, in about 30% of these samples the enrichment level was below 100%. This observation allows the use of the invention for diagnosis, specially in ESCA-type samples, where conventional diagnosis tests do not allow their identification as sub-fertile.

DETAILED DESCRIPTION OF THE INVENTION

The device suggested here (two compartments separated by a space where an attractant gradient is formed) has been designed as a function of the physical-chemical features of the attractant, where the length of the bridge (2 mm) and the incubation time of the set-up system (20 min) are adapted to use chemotactic concentration of progesterone (10 pM), enabling formation of a concentration gradient of this attractant.

The present device prevents mass flow of spermatozoa from one compartment to the other due to a physical effect of communicating vessels, thus assuring that the process is solely due to chemical action of the attractant. In other words, the mere connection of two compartments, where spermatozoa are placed in one of them, and the attractant in the other, in order to form a concentration gradient between both, does in no way guarantee assessment of the chemotaxis process. This is therefore guaranteed by a device having the feature of containing a hermetic closure comprising an elastic ring (4) seated on the top part of compartments 1a and 1b, a pair of plugs (3) seated on the elastic ring (4), a pair of openings (5) located above the elastic ring (4), which allow the air pushed by inserting the plug to exit to the exterior instead of pushing the fluid of 1b towards 1a. These invention adaptations are complemented by the device filling sequence.

Likewise, the proposed device use sequence or method in addition to diagnose physiologic status of a given semen sample dada, allows to select and isolate the best spermatozoa in the same procedure. The present device allows removal of the content or solution of compartment 1a and diagnosis of the physiologic status of the semen sample. To the effects of the present application, diagnose physiologic status of a sample means assessment of the chemotactic response capacity spermatozoa show in the presence of the physiologic attractant progesterone. Thus, net ratio of spermatozoa aggregated in the compartment containing progesterone (1a) is determined. Although said type of assay enables assessment of all types of sub-fertile samples, the invention shall be particularly useful to assess physiologic status of ESCA-type samples, since routine diagnosis assays do not allow identification their pathology.

The method is based on the feature of mammal spermatozoa of orienting their movement towards the production source of an attractant. This chemotactic capacity can also be exerted only by spermatozoa that have completed the "capability" process, a condition enabling them to fertilize the ovule. Therefore, the content of compartment 1a may also be used to select and/or separate spermatozoa capable of fertilizing ovules, where spermatozoa thus selected may be employed in the assisted fertilization techniques.

It is essential that the device consists of two compartments, one where spermatozoa are placed and the other for the attractant, in order to create an attractants concentration gradient.

After some time, capable spermatozoa go chemotactically towards the attractant source and aggregate in the compartment containing the attractant (1a), that is, in the latter an enrichment of capable spermatozoa shall be found, compared to the original semen sample. Thus, selection and aggregation of capable spermatozoa is performed physiologically by chemotaxis-mediated recruitment.

Figure 13:
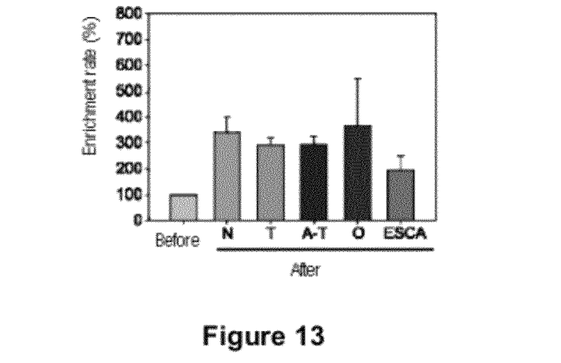
Figure 14:
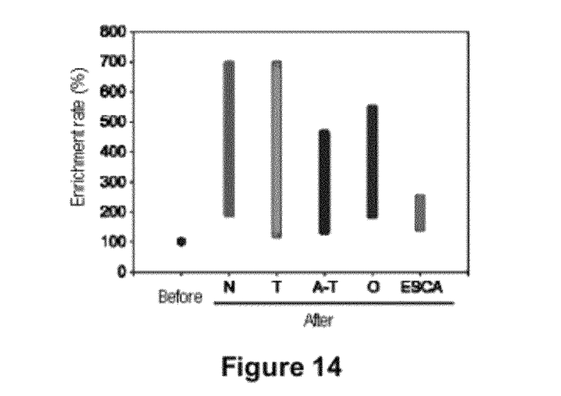

With this device, an enrichment of capable spermatozoa of up to 600% superior to the original semen sample can be obtained. Said enrichment was verified determining the ratio of spermatozoa performing the pharmacologically induced acrosome reaction, a procedure known as capacitation indicator (FIGS. 13 and 14).

The present device combines a disposition in two compartments with an attractant gradient, and dimensions adapted for an attractant effective at low concentrations, for example values between 1 and 100 pM progesterone, thus obtaining high efficiency in selection of the best spermatozoa, those capacitated.

In a preferred embodiment, the device may have particular dimensions adapted to progesterone features (its capacity to diffuse and form a concentration gradient, and its effectiveness at low concentrations). For example, the size of the connecting bridge between both compartments may be of about 2 mm diameter by about 2 mm long.

Since it is a communicating vessel system device, at the time of placing a liquid in one of the compartments, the fluid tends to pass to the other compartment through the bridge until the volume heights are equal. This phenomenon is not desirable, since it breaks the attractant gradient formation, and thus conveys mechanically, that is non-physiologically, spermatozoa towards the attractant-containing compartment.

To prevent the latter problem, the device is provided with a hermetic closing system. Optionally, both device compartments have a conical base, where the bridge connector insertion between both compartments is above said cone. The conical base allows dead or low movement spermatozoa decant to the bottom of the tube due to simple gravity, preventing them from being drawn to the bridge and the other compartment by the faster chemotactic spermatozoa.

The present device confers the necessary hermetic conditions to prevent fluid movement is such a small system, and also prevent external contamination.

Summarizing, the device suggested herein allows diagnosing and selecting the best spermatozoa in only one step, in a simple, low cost, and highly efficient way that can be done in less than one hour by personnel with elemental laboratory knowledge.

In relation to the applications of the suggested device, its use for diagnosis of physiologic status of given semen sample is provided, at the same time recruiting the best spermatozoa for later use to improve fertilization rates.

It must be noted that the suggested method checking tests were performed using a methodology to determine a very sophisticated chemotactic response by spermatozoa, that requires a costly equipment and highly trained personnel.

Figure 1A:
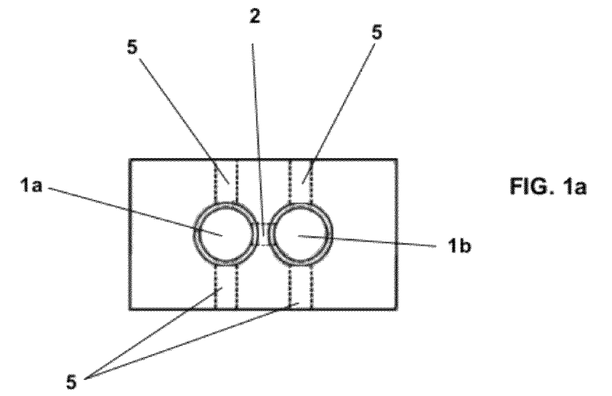
FIGS. 1a, 1b and 1c illustrate respective top, front, and lateral view of the device of the present invention.
Figure 1B:
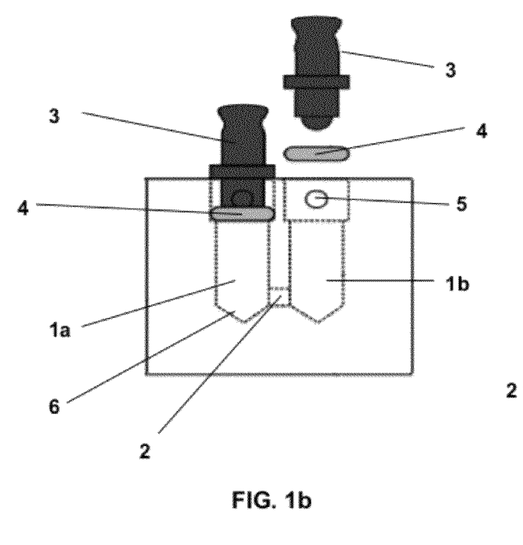
Figure 1C:
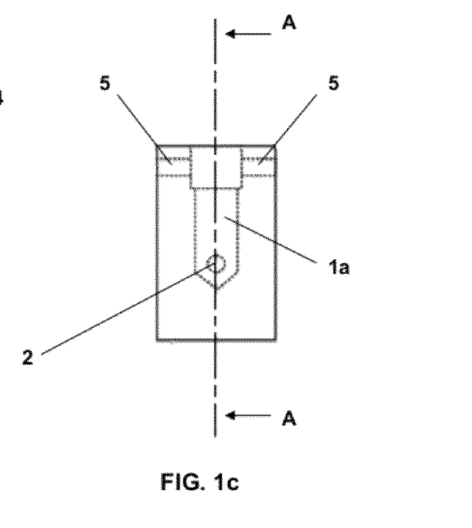
Figure 2:
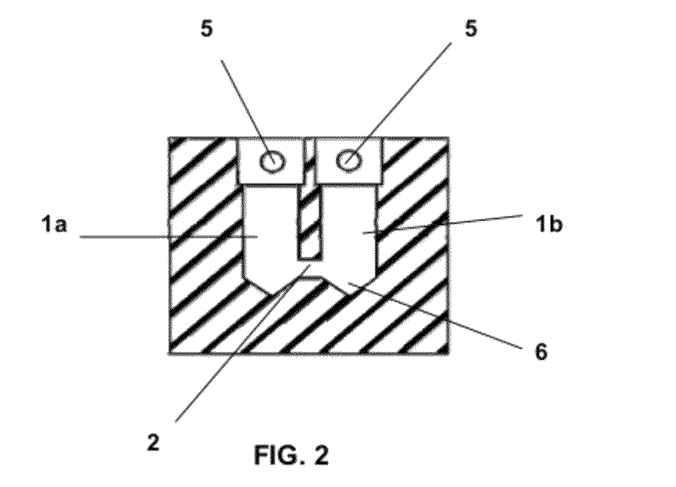
FIG. 2 shows a cut according to line A-A of FIG. 1c.
Figure 3:
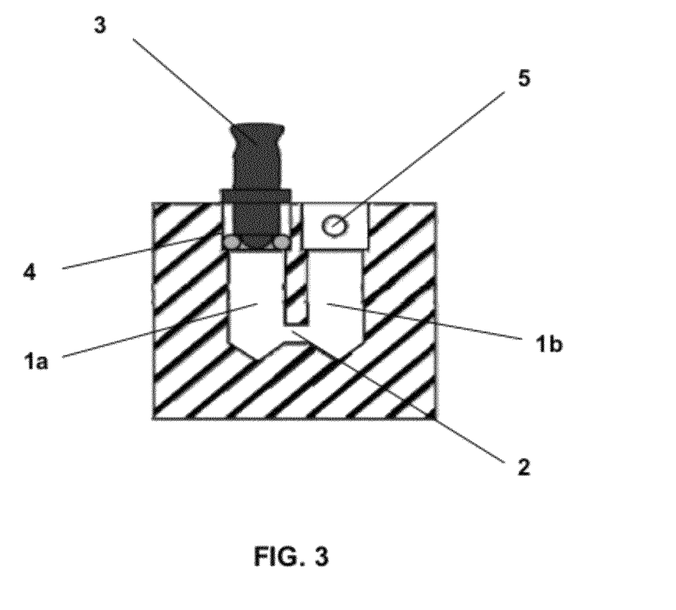
FIG. 3 shows a cut according to line A-A of FIG. 1c incorporating a closing means.

In FIGS. 1 to 3 it is noted that the device, preferably manufactured in acrylic, of biocompatible material and necessarily transparent for an efficient use of the, consists of two cylindrical vertical compartments "1*a*" and "1*b*", of a preferable length of 12 mm by 4 mm diameter (equivalent capacity of 130 μl), connected by a tube or bridge "2", 2 mm long by 2 mm diameter (equivalent capacity of 20 μl).

In one of the compartments, for example "1*b*", the suspension containing spermatozoa is placed, and in the, "1*a*", the attractant is placed. Along the bridge 2, an increasing attractant concentration gradient is formed, allowing the selection of spermatozoa by chemotaxis, which aggregates in the attractant compartment 1*a*.

In preferred embodiment, the present device dimensions are adapted to the use of progesterone as attractant, and to minimize the volume placed in each compartment. It shall be evident to an expert in the art that the attractant may be any chemoattractant effective at low concentrations, for example concentrations in the order of picomoles.

Although the device design allow the use thereof employing progesterone as attractant, an expert in the art knows that any other known attractant may be used without altering the spirit of the present invention.

Since it is a communicating vessel system, an important aspect is to prevent fluid flow through the bridge 2 while filling or emptying compartments "1*a*" and "1*b*". This unwanted effect may break the attractant gradient, thus loosing the device function principle, or else mechanically convey the content of a compartment to the other, which also notably diminishes the efficiency of the device.

In order to prevent said inconveniences, means are provided to hermetically close compartments, thus combining adaptation of the present device with a particular closing sequence.

In each compartment, "1*a*" or "1*b*", said closing means comprise a plug with a projection "3" seated on an elastic rubber ring "4", on which the hermetic closing occurs. In addition, an opening "5" in the top part of each compartment "1*a*" and "1*b*" is provided between the plug "3" and the rubber ring "4", which allows constant outflow of the contained air therein while placing plug "3", in order to hermetically close compartment "1*a*" or "1*b*".

Another detail of the device is the conical finishing "6" of each compartment base, located under the bridge connection, where the gradient where swimming spermatozoa migrate is formed. This adaptation allows dead or low mobility spermatozoa decant by gravity to the bottom of the compartment, thus preventing them from being drawn by the mobile spermatozoa into the bridge.

As related the way of using the present device, operation is described below:

Separation of mobile spermatozoa (S) of seminal plasma is done by the Percoll technique. A volume of about 2 ml semen is used, which is deposited on 1 ml Percoll gradient (lower layer: 500 μl Percoll 95%, upper layer: 500 μl of Percoll 47.5%, in HAM-F10). After centrifuging 20 minutes at 1800 rpm, the cell pellet is recovered and washed twice by centrifugation for 7 min at 1000 rpm, with HAM-F10 medium. Finally, the recovered pellet is suspended in 1 ml of HAM-F10 medium, cell count is performed in a cell count chamber, and volume is adjusted in order to obtain a concentration of 8 million S/ml. S capability is increased in HAM-F10 medium supplemented with 1% human serum albumin (HSA) for 4 hours a 37° C., under 5% $CO_2$ atmosphere in air.

When capacitation time is finished, S concentration is adjusted in order to obtain 6 million mobile S/ml, and two devices are set up as described in the preceding section (FIGS. 1-3), one without attractant as negative control, and the other with progesterone as attractant.

To set up the device control, a device as described in FIGS. 1 to 3, proceed as follows: 1) the plug is placed in compartment 1*a*, where culture medium (HAM-F10/1%HSA) is placed, 2) the bridge linking both compartments is filled with culture medium, 3) S suspension is placed in compartment 1*b* (130 μl of the solution of 6 million mobile S/ml) and this compartment is closed with the plug, 4) compartment 1*a* is unplugged and filled with culture medium (130 μl).

For device set up with the attractant, another device is prepared as described in FIGS. 1 to 3, like the device control but replacing culture medium with a 10 pM Progesterone solution diluted in culture medium. Once both devices are set up ("Control" and "Attractant"), they are incubated for 20 minutes at 37° C., under 5% $CO_2$ atmosphere in air.

To take the device apart and recover the best spermatozoa, the compartment solution (1*a*) containing culture medium or attractant is removed. On the spermatozoa suspension removed from compartment 1*a* of both devices (control and attractant) cell count is performed in a cell count chamber. Then the difference in percentage of S found in each of these two compartments is determined, which enables to value net percentage of S migrating to the attractant-containing compartment ("Δ").

Once the device design stage is finished, a series of experiments then proceeded in order to define experimental conditions of the use thereof, and then to proceed with method validation.

Figure 4:
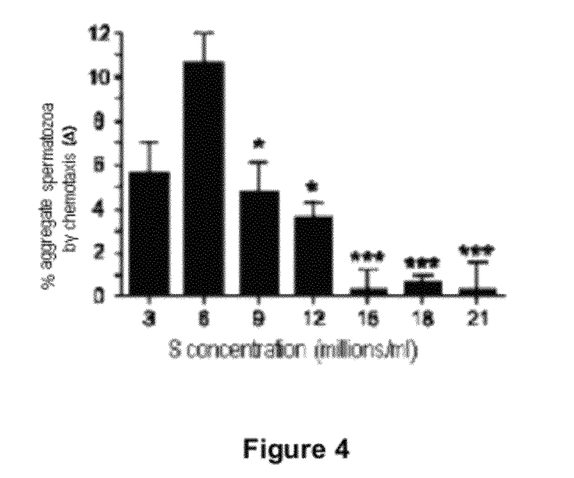
FIG. 4 shows a graph of optimum spermatozoa concentration (S) used in sperm separation. Values depict Mean±SEM of percentage of spermatozoa aggregated in compartment 1a by chemotaxis (n=3). *$p<0.05$; ***$p<0.001$ vs. 6 million S/ml.
Figure 5:
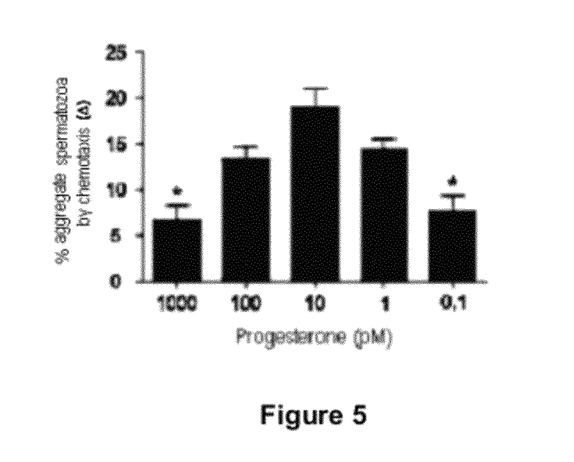
FIG. 5 shows a graph of Progesterone concentration used in sperm separation. Values depict Mean±SEM of percentage of spermatozoa aggregated in compartment 1a by chemotaxis (n=3). *$p<0.01$ vs. 10 pM of progesterone.
Figure 6:
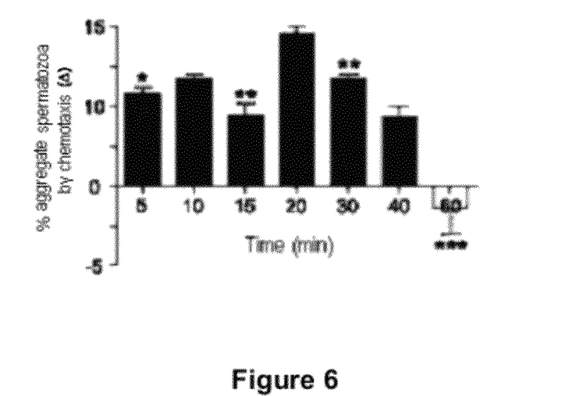
FIG. 6 shows a graph of incubation times employed for sperm separation. Values depict Mean±SEM of percentage of spermatozoa aggregated in compartment 1a by chemotaxis (n=3). *$p<0.05$, $p<0.01$, *$p<0.001$ vs. 20 min.

The best experimental conditions to obtain optimal sperm separation, (assessed as the difference "Δ" between the ratio of S aggregating in the compartment with culture medium and with attractant), were: 1) a suspension with a concentration of about 6 million S/ml (FIG. 4), 2) a concentration of about 1 to 100 pM progesterone (FIG. 5), and 3) a device incubation of about 20 minutes (FIG. 6).

Figure 7:
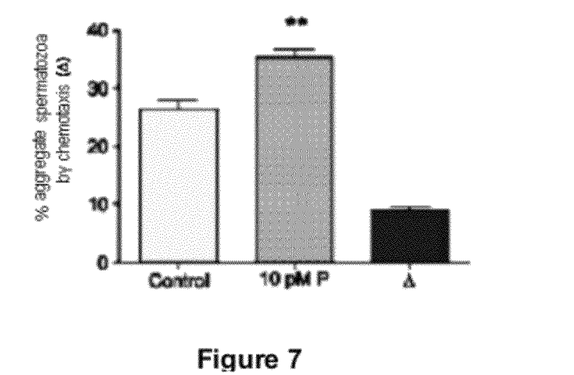
FIG. 7 shows a graph of sperm separation using the device designed by us in conditions to obtain a maximal response (6 million S/ml, 10 pM progesterone, and 20 minutes incubation), described above, and illustrated in FIGS. 4 to 6, respectively. Values depict Mean±SEM, of percentage of aggregated spermatozoa in compartment 1a by chemotaxis. Ratio of aggregated spermatozoa by chemotaxis in the compartment with progesterone is of about 10% (A; n=5). **$p<0.01$ vs. Control.
Figure 8:
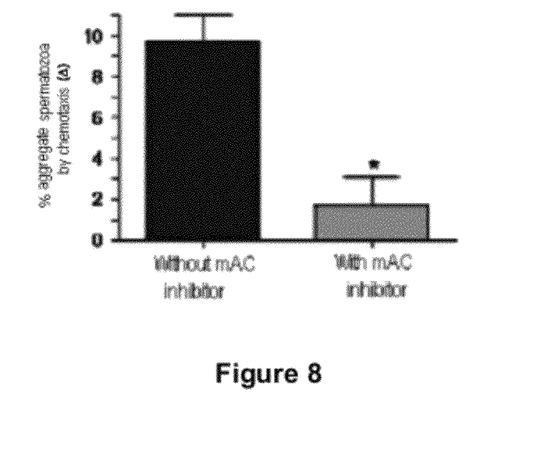
FIG. 8 shows the percentage of aggregated spermatozoa (Mean±SEM; n=3) in compartment 1a by chemotaxis when cells were previously treated with the inhibitor (ddAdo) of an enzyme (mAC) participating in the chemotactic signal. In the presence of the inhibitor, no sperm aggregation due to chemotaxis is seen (*p<0.05).
Figure 9:
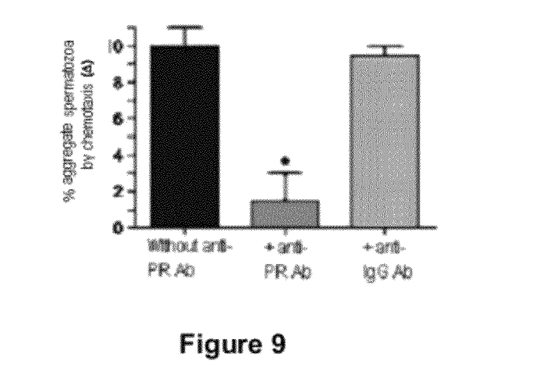
FIG. 9 shows percentage of aggregated spermatozoa (Mean±SEM; n=3) in compartment 1a by chemotaxis when cells were previously treated with antibody "c262" against progesterone receptor (anti-PR Ab). In the presence of antibody, spermatozoa do not aggregate in compartment 1a (*p<0.05), while treatment with non-specific antibody (anti-IgG Ab) does not prevent sperm aggregation.
Figure 10:
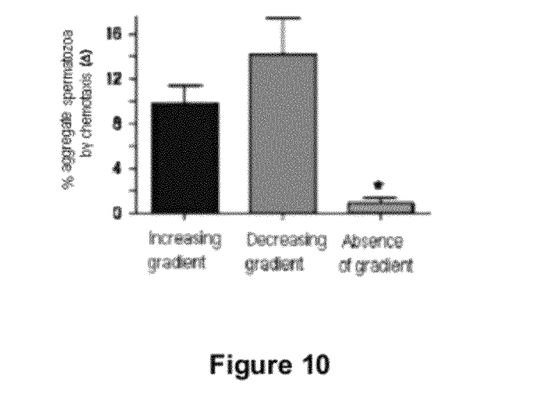
In FIG. 10, percentage of aggregated spermatozoa in the presence of an increasing gradient of progesterone was similar to one found in a decreasing gradient of attractant, while in the absence of gradient of progesterone (equal concentration of hormone in both compartments 1a and 1b) sperm aggregation is reduced (*p<0.05).
Figure 11:
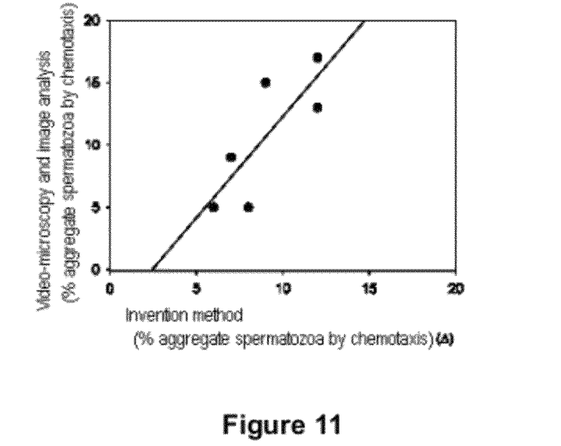
FIG. 11 compares proportion of aggregated spermatozoa by chemotaxis with the inventive method, with percentage of chemotactic spermatozoa determined by video-microscopy and image computer analysis. A high and significant correlation is found between both methods. (r=0.794; p<0.05; n=6).
Figure 12:
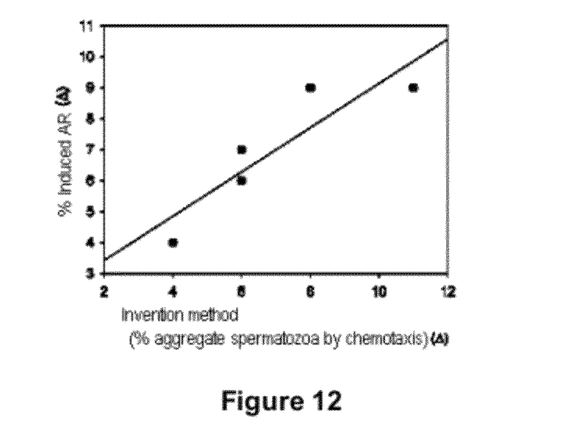
FIG. 12 shows correlation between proportion of spermatozoa with induced acrosome reaction (AR) and proportion of aggregated spermatozoa by chemotaxis with the inventive method. Values depict Mean±SEM (n=5). (r=0.947; p<0.05; n=5).

Thereafter, method validation for diagnosis (based on chemotactical response of S) was done in three ways: 1) by inhibition of chemotactical response, inhibiting the mAC enzyme, which participates in the chemotactical signaling, 2) by inhibition of chemotactical response, blocking the progesterone receptor located on the sperm cell membrane, 3) by comparison with a decreasing progesterone gradient and exposure to the absence of progesterone gradient, 4) by comparison with determination of chemotaxis by video-microscopy, and 5) by comparison with induced acrosome reaction level (AR). Sperm chemotaxis-mediated separation towards progesterone enabled the observation of a spermatozoa subpopulation significantly migrating towards Progesterone (9±0.4%; $p<0.01$; FIG. 7 "Δ"). Such cell population correlated with the percentage of chemotactical spermatozoa assessed by video-microscopy ($r=0.79$, $p<0.01$; FIG. 11 and of induced AR ($r=0.94$, $p<0.05$; FIG. 12). Ratio of aggregated spermatozoa by an increasing progesterone gradient was similar to the observed with a decreasing progesterone gradient, with no sperm aggregation observed in the absence of progesterone gradient ($p<0.001$; FIG. 10). Sperm aggregation by chemotaxis was prevented by inhibition of an enzyme participating in the cell process, and also by blocking progesterone receptor activity ($p<0.05$; FIGS. 8 and 9).

Method validation to select the best spermatozoa was done by calculating percentage of increase in the induced acrosome reaction level value, in population of obtained spermatozoa after sperm separation, and in comparison with the value obtained in the spermatozoa sample before separation, considering the latter as 100%. Results showed that the enrichment level in capable spermatozoa after sperm separation may reach up to 600% (FIGS. 13 and 14).

In summary, the device design involving adaptation of dimensions to the used attractant, a hermetic closure, and the definition of the precise filling and emptying sequence, which provide unique features to this device and the procedure, results in a substantial improvement in diagnosis efficiency and selection or separation of the best spermatozoa.

The invention claimed is:

1. A device for diagnosis of physiologic status and/or selection of spermatozoa of a semen sample based on a concentration gradient of an attractant molecule, the device comprising:
 two adjacent, communicated compartments (1a, 1b), each of the compartments comprising an opening, an upper portion and a lower portion;
  each upper portion comprising an air output duct (5) and an opening, each air output duct being transversally placed below each opening, and
  each lower portion comprising an end, each end having a conical base (6);
 a connection duct or bridge between the compartments (2), the connection duct or bridge being placed between the compartments at the lower portion above each of the conical bases; and
 separate closing means for each compartment, each closing means comprising a plug (3) and an elastic ring (4);
 wherein when the closing means is placed at a closed position in the opening and upper portion of each compartment, each of the elastic rings sits below each air output duct allowing the exit of air.

2. The device according to claim 1, wherein each air output duct are present at each communicated compartment and each air output duct runs transversally through the bore of each compartment.

3. The device according to claim 1, wherein the air output duct allows air inside the compartment either to exit while the plug is being inserted or to enter while the plug is being removed, thus avoiding breakage of the attractant gradient in the connection duct or bridge.

4. The device according to claim 1, wherein the compartments are formed within a transparent body made of a biocompatible material.

5. The device according to claim 1, wherein said compartments (1a, 1b) are 12 mm in length and 4 mm in diameter including each of the conical bases and have a capacity equivalent to 130 μl, and the duct or bridge (2) is 2 mm in length and 2 mm in diameter with a capacity equivalent to 20 μl.

6. The device according to claim 1, wherein the conical base allow dead or low movement spermatozoa to decant to the conical base due to simple gravity, preventing the dead or low movement spermatozoa from being drawn into the connection duct or bridge and the adjacent compartment by faster chemotactic spermatozoa.

* * * * *